United States Patent [19]

Mericle

[11] 4,428,376
[45] Jan. 31, 1984

[54] PLASTIC SURGICAL STAPLE

[75] Inventor: Robert W. Mericle, Bridgewater, N.J.

[73] Assignee: Ethicon Inc., Somerville, N.J.

[21] Appl. No.: 388,567

[22] Filed: Jun. 14, 1982

Related U.S. Application Data

[63] Continuation of Ser. No. 146,943, May 2, 1980, abandoned.

[51] Int. Cl.³ .................. A61B 17/08; A61B 17/04
[52] U.S. Cl. ......................... 128/335; 128/334 R; 411/457
[58] Field of Search .......... 128/325, 326, 335, 334 R, 128/337; 227/19, 119, DIG. 1, 83; 411/457, 460, 468, 469, 471, 472

[56] References Cited

U.S. PATENT DOCUMENTS

| | | | |
|---|---|---|---|
| 1,728,316 | 9/1929 | Von Wachenfeldt | 128/334 R |
| 2,881,762 | 4/1959 | Lowrie | 128/337 |
| 2,887,110 | 5/1959 | Roeschmann | 128/334 R |
| 3,068,870 | 12/1962 | Levin | 227/DIG. 1 |
| 3,604,425 | 9/1971 | Le Roy | 227/DIG. 1 |
| 3,620,218 | 11/1971 | Schmitt et al. | 128/334 |
| 3,643,851 | 2/1972 | Green et al. | 227/19 |
| 3,646,801 | 3/1972 | Caroli | 128/334 R |
| 3,739,773 | 6/1973 | Schmitt et al. | 128/334 |
| 3,873,016 | 3/1975 | Fishbein | 227/83 |
| 3,875,648 | 4/1975 | Bone | 227/19 |
| 4,014,492 | 3/1977 | Rothfuss | 227/19 |
| 4,021,890 | 5/1977 | Kurosaki | 411/472 |
| 4,060,089 | 11/1977 | Noiles | 128/325 |
| 4,109,844 | 8/1978 | Becht | 227/120 |
| 4,162,678 | 7/1979 | Fedotov et al. | 128/334 R |

FOREIGN PATENT DOCUMENTS 790997 11/1935 France .................. 128/335

*Primary Examiner*—C. Fred Rosenbaum
*Assistant Examiner*—C. W. Shedd
*Attorney, Agent, or Firm*—Robert L. Minier

[57] ABSTRACT

A one-piece, self-locking, molded plastic staple useful as a tissue fixation device in surgical procedures. The staple has opposed, pointed, L-shaped legs hinged to a horizontal bridging member having expanding cam surfaces on each end. Each leg has an extending cam follower which traverses the cam surface and engages the end of the bridging member when the staple is closed by rotating the legs 90 degrees. The staples may be extruded or molded of absorbable or nonabsorbable polymeric materials.

25 Claims, 12 Drawing Figures

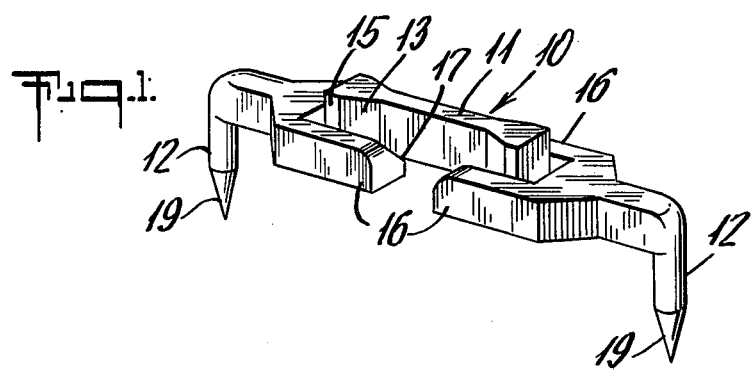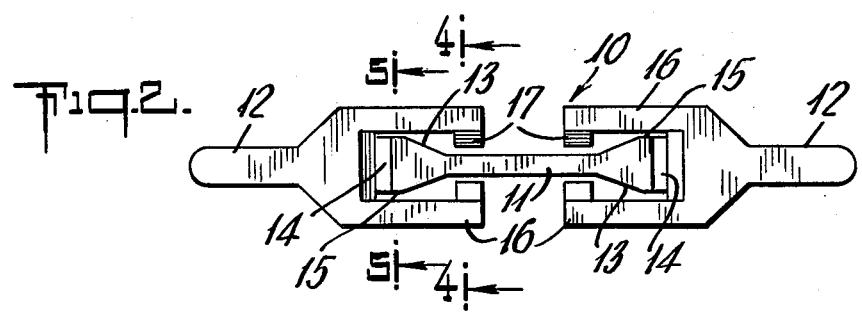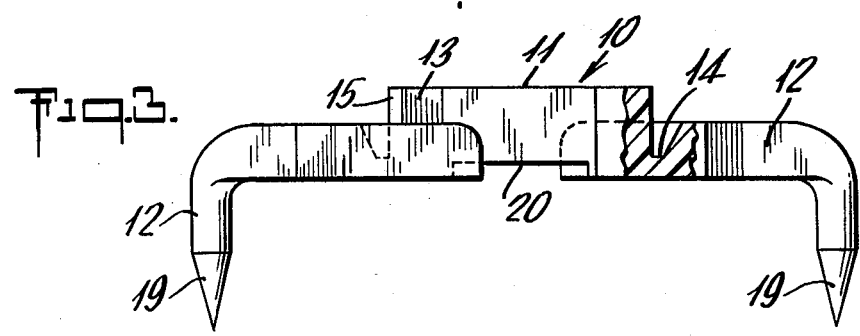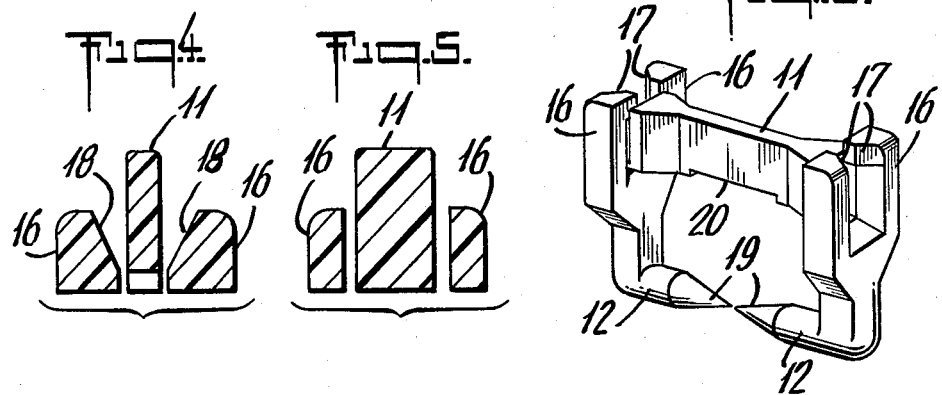

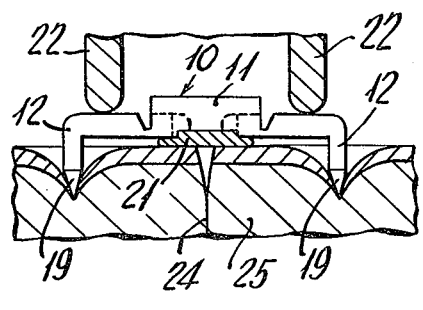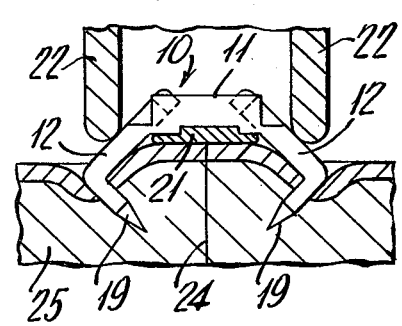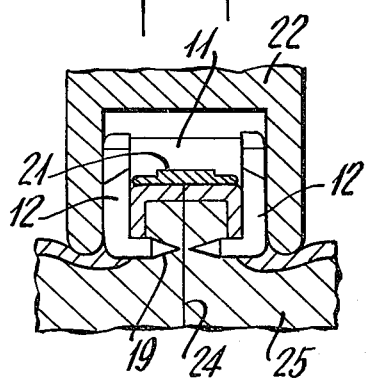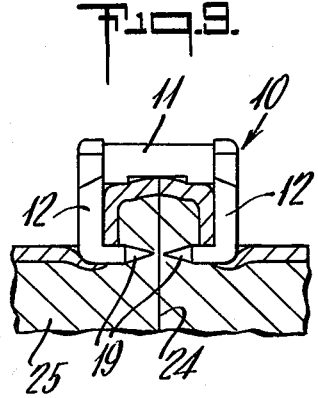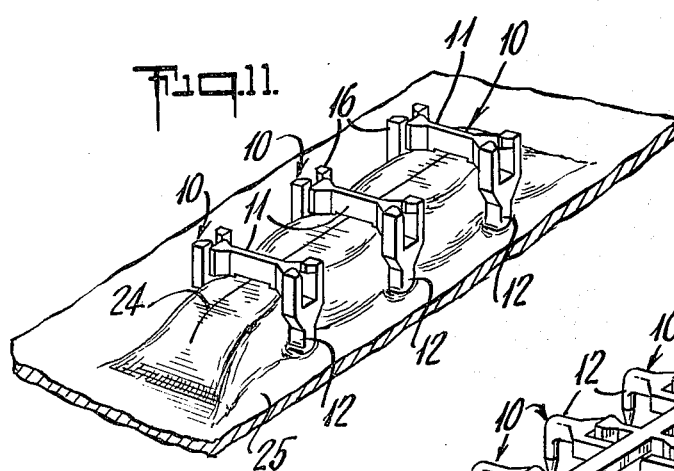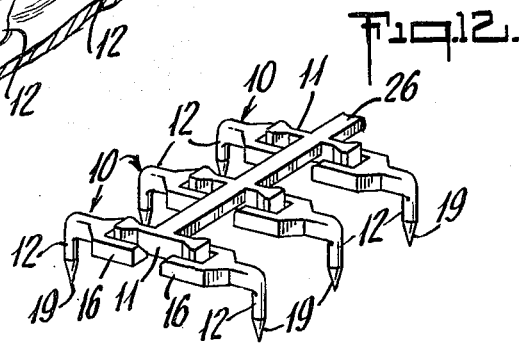

PLASTIC SURGICAL STAPLE

This is a continuation, Ser. No. 146,943, filed May 2, 1980 now abandoned.

BACKGROUND

In recent years, surgical staples have come into wide use as an alternative to sutures in closing incisions of skin, fascia, and internal organs. Staples have an advantage over sutures in some applications due to the speed and ease with which staples may be placed. In addition, special stapling instruments have been designed which place an entire row or ring of staples in a single operation to further simplify and speed up the surgical procedure.

Surgical staples currently in use are fabricated of tantalum or stainless steel wire having sufficient tensile strength and bending modules to assure that the staple will remain closed after it has been set in place. Although it has long been recognized that the staples made of plastic or polymeric materials would be desirable for use in surgical applications, the development of such staples has been difficult due to inherent resiliency of such materials. Staples of known plastic compositions and of the same configuration as a metallic staple do not have sufficient strength and bending modulus to stay closed after being set in place. One approach to utilizing plastic materials in surgical stapling procedures has been to provide cooperating mechanical means to secure the staple in its set configuration. U.S. Pat. No. 2,881,762 proposed a circular, open ring-type staple wherein the ends were designed to pierce the tissue, overlap and lock to form a closed ring through the tissue similar to a knotted suture. More recently, a two-piece staple was suggested in U.S. Pat. No. 4,060,089 wherein a pronged fastener strip pierced the tissue and a cooperating retainer strip gripped the prongs on the opposite side of the tissue. This device is limited in its application to situations where access to both sides of the tissue is available, and a special tool is required to apply the device.

It is an object of the present invention to provide a plastic staple which functions in a manner analagous to that of a metallic staple, i.e., a one-piece device which is applied from one side of the tissue. It is a further object of the present invention to provide a plastic staple which can be set with a tool of conventional design. It is yet a further object of the present invention to provide plastic staples fabricated of biologically absorbable polymers as well as of conventional nonabsorbable polymers. These and other objects of the present invention will be apparent from the ensuing description and claims.

SUMMARY

A one-piece, self-locking, molded plastic staple is provided which comprises a central beam having outward and downward L-shaped staple legs secured to each end thereof by integral hinge means. The central beam has expanding side wall cam surfaces at each end thereof, and each leg has a resilient arm extending over the cam surface of the central beam and terminating in an inward facing cam follower.

As the staple is closed by rotating the staple legs about the hinge means, the resilient arms rotate and are deflected as the cam followers traversed the cam surface until the cam follower overrides the end of the central beam, whereupon the arms close and engage the ends of the beam to lock the staple legs in their rotated position. The staple is emplaced in the tissue with a conventional stapling mechanism comprising an anvil and forming die. The anvil supports the central beam of the staple while the forming die acts upon each leg member, causing the legs to rotate about the hinge means. As the staple closes, the legs pierce the tissue and form a box-like configuration enclosing a segment of tissue with the ends of the staple leg approaching one another within the tissue.

The staple may be machined or molded of any suitable polymeric material including both biologically absorbable and nonabsorbable compositions. Preferred absorbable materials include polymers of lactide and glycolide. Preferred nonabsorbable materials include nylon and polypropylene.

DESCRIPTION OF THE DRAWINGS

FIG. 1 is a view in perspective of a surgical staple according to the present invention.

FIG. 2 is a plan top view of the staple of FIG. 1.

FIG. 3 is a side elevational view in partial section of the staple of FIG. 1.

FIG. 4 is a sectional view through line 4—4 of FIG. 2.

FIG. 5 is a sectional view through line 5—5 of FIG. 2.

FIG. 6 is a view showing the staple of FIG. 1 in its relation to the forming anvil, the forming die and the wound which is to be closed.

FIG. 7 is a view similar to FIG. 6 showing the staple in the process of being formed.

FIG. 8 is a similar view showing the staple completely formed and closing the wound.

FIG. 9 is a view similar to FIG. 5 showing the wound after the forming tool has been removed.

FIG. 10 is a view in perspective showing the staple of FIG. 1 in its fully closed and locked position.

FIG. 11 is a perspective view of a wound properly closed by a plurality of staples according to the invention.

FIG. 12 is a view in perspective showing a plurality of the staples of FIG. 1 on a stringer for use in a repeating stapler unit.

DESCRIPTION

With reference to FIGS. 1-3, there is illustrated staple 10 of the present invention comprising center beam 11 and staple legs 12 which are joined at their base through hinges 14. Center beam 11 has expanding side walls forming cam surfaces 13 and dwell surfaces 15 at each end thereof. Extending from the hinge end of each staple leg are arms 16 which overlie cam surfaces 13 and terminate in inward facing cam followers 17. The distal ends of staple legs 12 are sharpened to form tissue piercing points 19. The base of beam 11 is optionally channeled at 20 as illustrated to form an anvil guide as further described below.

Cam followers 17 are beveled at 18 as illustrated in FIG. 4 to provide a cam face angled for engagement with the cam surfaces of the center beam. FIG. 4 is a view of FIG. 2 in cross section through line 4—4.

FIG. 5 is a view in cross section through line 5—5 of FIG. 2 and illustrates the relative dimensions of central beam 11 and arms 16. Beam 11 preferably has a height to width ratio of at least about 1.5 to provide the desired structural rigidity.

The emplacement of staple 10 to approximate the tissue of a skin wound is illustrated progressively in FIGS. 6 through 9. The staple is closed by use of a conventional staple-forming tool which includes anvil 21 and a bridging die 22 as illustrated in part in FIGS. 6–8.

Referring now to FIG. 6, staple 10 is positioned in the forming tool by suitable means with center beam 11 supported by anvil 21 and the extremities of die 22 abutting staple legs 12. Anvil 12 includes a central stepped section to engage channel 20 of beam 11 and assure that the staple is centered on the anvil prior to closure. The forming tool and staple are placed directly over wound 24 in tissue 25. Since the staple legs extend below the level of the anvil, the legs are caused to make initial contact with and may penetrate the tissue slightly as the forming tool is moved into position.

The staple is closed and the would secured by lowering die 22 beyond anvil 21 as illustrated in FIGS. 7 and 8. In FIG. 7, as the staple begins to close, legs 12 penetrate the skin in a tissue gathering arc and arms 16 rotate upward with cam followers 17 riding against cam surfaces 13 of beam 11. Beveled face 18 of the cam follower conforms to the angle of the cam surface and permits easier passage of the arms during this motion. As arms 16 rotate upward, opposing arms extending from each leg are forced apart by the camming action. As the degree of rotation exceeds about 90 degrees, the cam followers traverse dwell surface 15 and override the end of beam 11, whereupon the arms snap back to their original spaced relationship and the cam followers engage the end surface of beam 11 as best illustrated in FIG. 10. The staple is thereupon securely locked in its closed position. Once the staple is so locked, die 22 is raised and the forming tool removed leaving the staple securely fastened in the tissue across the wound with the edges of the wound properly everted as illustrated in FIG. 9. FIG. 11 illustrates a complete incision properly closed with a series of staples in accordance with the present invention.

Dwell surfaces 15 are optional but preferably included to provide mass and strength to the edges of the end walls of beam 11, and to eliminate the possibility of the end wall failing under stress once the arms of staple legs are engaged in the locked position. For similar considerations, bevel 18 of the cam followers does not extend to the base of arm 16 in order to assure the structural integrity of the cam follower.

As illustrated and described above, the external parts of the staple may generally be of a rectangular configuration while the tissue piercing segments of the staple legs are preferably of circular cross section for ease of penetration and to minimize tissue trauma.

The staples of the present invention may be molded as a series of staples joined by stringer as illustrated in FIG. 12. Stringer 26 permits a plurality of staples to be loaded into a repeating staple setting instrument which, in addition to the setting die and anvil previously described, also includes knife means for severing individual staples from the stringer as the staples are moved to the setting position in the instrument. The instrument preferably also provides means for collecting the severed stringer pieces to prevent their accidental loss into the wound site.

In FIG. 12, the staples are widely spaced on the stringer for clarity of illustration while in actual practice, the staples would be in close proximity. Other methods for providing a plurality of joined staples may also be used as, for example, molding a plurality of staples with adjacent arms tacked together at one or two spots. Individual staples may be severed from such a molding without concern for collecting severed stringer pieces.

While the staple of the present invention has been described and illustrated in a skin closure application, the staple may be used for closing fascia or internal organs as well. Since the staple is adapted for use with staple emplacement tools of a conventional design, the use of individual staples in cartridge fed, repeating stapling instruments or in instruments which set a plurality of staples in a straight line or in a circle with a single firing is also included within the scope of this invention. It is understood that some modification of existing stapling instruments may be required to physically accommodate the staples of the present invention, but such modification is well within the present skill of surgical instrument manufacturers.

The staples of the present invention may be constructed in sizes corresponding to the size of conventional metallic staples. In an average size staple, the central beam may be from about 0.25 to 0.6 cm in length, while the L-shaped staple leg members and arm extensions are sized proportionately as illustrated, for example, in FIG. 1.

The staples may be fabricated by any suitable plastic forming technique including extrusion and injection molding depending upon staple design and composition of material which may be any of polymeric compositions known to be biocompatible in surgical applications. Nylon, polypropylene, polyester and polysulfone are illustrative of materials which may be used to form nonabsorbable staples. Homopolymers and copolymers of lactide, glycolide and p-dioxanone are illustrative of materials which may be used to fabricate absorbable staples for internal application. Other suitable polymeric compositions are known to those familiar with the art and may also be used in accordance with the present invention.

Nonabsorbable staples of, for example, polypropylene or nylon may be used in internal applications where absorption is not an important factor. Where such staples are used externally, they are easily removed after the wound has sufficiently healed by inserting an appropriate tool under the center beam and forcing the staple legs back to their original position as illustrated in FIG. 1. During such removal, the resilient arms of the staple legs twist until the cam followers are forced past the end of the center beam, allowing the staple legs to pivot about the hinge point and return to their original position.

The preceding description and the Figures of the illustration have been directed to a particularly preferred embodiment of the present invention, and many variations thereof which will be apparent to those skilled in the art are included within the total scope of the present invention. For example, in addition to permissible variations mentioned above, it will be apparent that the details of the staple leg cam and locking means may be varied consiberably. Each staple leg may, for example, employ only a single arm extension and cam follower, or the other suitable staple leg cam and locking means may be employed. In yet other variations, the center beam and staple legs may be molded as individual pieces and joined together by means of hinge pins extending through the arms of the staple leg and into the sidewall near the end of the center beam. These and other structural variations are contemplated by and included within the scope of the present invention.

What is claimed is:

1. A self-locking surgical staple comprising a center beam, said center beam having opposing side walls, two staple legs extending from each end of said center beam, said staple legs being joined to said center beam by hinge means adapted to permit said staple legs to rotate relative to said center beam, said staple legs terminating in tissue-piercing segments which assume substantially end-to-end alignment when said staple legs are rotated relative to said center beam, and cam means cooperatively disposed on said side walls of said center beam, said cam means being for locking legs adapted to lock said staple legs in position with said tissue-piercing segments in substantially end-to-end alignment when said staple legs are so rotated.

2. The staple of claim 1 wherein said center beam has opposing end walls and said hinge means comprises an integral web extending from each of said end walls to said staple legs.

3. The staple of claim 2 wherein said center beam has a top surface and opposing base, and said web extends from said base.

4. The staple of claim 2 wherein the distance between said end walls is from about 0.25 to 0.6 cm.

5. The staple of claim 1 wherein the cam means includes at least one side wall cam surface expanding toward each end of the said beam.

6. The staple of claim 5 wherein said cam means further includes at least one arm extending from each staple leg over a cam surface of a side wall and terminating in an inward facing cam follower confronting said side wall.

7. The staple of claim 6 wherein said cam followers include a locking surface and are adapted to override the cam surfaces and ends of said center beam as said staple legs are rotated relative to said center beam, whereupon said locking surface engages the end wall of said center beam to lock the staple legs in their rotated position.

8. The staple of claim 6 wherein said cam followers are beveled to provide a face conforming to the angle of said cam surfaces.

9. The staple of claim 1 wherein said cam means includes
   a pair of expanding side wall cam surfaces at each end of said center beam, and
   a pair of arms extending from each staple leg over said cam surfaces and terminating in an inward facing cam follower confronting the side wall of said center beam.

10. The staple of claim 1 comprising an absorbable polymeric composition.

11. The staple of claim 10 wherein said absorbable polymeric composition is a homopolymer or copolymer of lactide, glycolide, or p-dioxanone.

12. The staple of claim 1 comprising a nonabsorbable polymeric composition.

13. The staple of claim 12 wherein said nonabsorbable polymeric composition is selected from the group consisting of nylon, polyester, polypropylene, and polysulfone.

14. A one-piece, self-locking, surgical staple comprising
    a center beam and
    two L-shaped staple legs extending from each end thereof,
    said center beam comprising a rectangular member having a top surface and a base, opposing end walls, and opposing side walls, said side walls including at least one expanding cam surfaces at each end of said center beam,
    said staple legs being joined to said end walls by integral hinge means at one end and terminating at the other end in tissue-piercing segments depending at right angles from the plane of the base of said center beam,
    at least one resilient arm extending from the hinge end of each staple leg over an expanding cam surface of said center beam,
    a cam follower extending from the distal end of said arm and confronting the side wall of said center beam,
    said cam follower being adapted to cooperatively cam on said expanding cam surface and to override the end wall of said center beam when said staple legs are rotated about said hinge means,
    said resilient arms deflecting as said cam follower cams on said cam surface and until said cam follower overrides the end of said center beam,
    whereupon said arms close and engage the ends of said center beam, thereby locking said staple legs in the rotated position.

15. The staple of claim 14 wherein said hinge means comprises a web extending from the base of said center beam to the corresponding base of said staple arm.

16. The staple of claim 14 wherein said side walls include opposing cam surfaces at each end thereof.

17. The staple of claim 16 wherein each staple leg includes a pair of resilient arms extending over opposing cam surfaces at each end of said center beam.

18. The staple of claim 14 wherein said cam followers are beveled to provide a face conforming to the angle of said cam surface.

19. The staple of claim 14 wherein said cam surface includes a dwell surface adjacent the end wall of said center beam.

20. The staple of claim 14 wherein the base of said center beam is channeled.

21. The staple of claim 14 wherein the tissue piercing segments of said staple legs have a circular cross section.

22. The staple of claim 14 wherein the center beam has a height to width ratio of at least about 1.5.

23. In combination with a stapling tool having a forming anvil and a cooperative forming die, a self-locking, plastic surgical staple comprising
    a center beam and
    two staple legs extending from each end thereof,
    said staple legs being joined to said center beam by hinge means adapted to permit said staple legs to rotate relative to said center beam,
    said staple legs terminating in tissue piercing segments which assume substantially end-to-end alignment when said staple legs are rotated relative to said center beam, and
    cam means cooperatively disposed on said center beam and said staple legs adapted to lock said staple legs in position with said tissue-piercing segments in substantially end-to-end alignment when said staple legs are so rotated,
    said forming anvil having a width substantially equal to the length of said center beam,
    said forming die having two downward projecting extremities spaced to engage the staple legs when the center beam is positioned on the anvil, the distance between said extremities corresponding substantially to the width of the staple after closure, said anvil and said forming die being adapted to close said staple by rotating said staple legs relative to said center beam, whereupon said cam means lock said staple legs in the closed position with the tissue piercing segments of said staple legs in substantially end-to-end alignment.

24. The combination of claim 23 wherein the tissue-piercing ends of the staple legs extend beyond the plane of the anvil when the staple is centered on the anvil prior to closure.

25. The combination of claim 23 wherein said center beam has opposing top and base surfaces, and staple centering guide means are cooperatively disposed on said base surface and said forming anvil.

* * * * *